(12) United States Patent
Cho et al.

(10) Patent No.: US 6,951,655 B2
(45) Date of Patent: Oct. 4, 2005

(54) PRO-MICELLE PHARMACEUTICAL COMPOSITIONS

(75) Inventors: Young W. Cho, Fremont, CA (US); Kwang-Ho Lee, Fremont, CA (US)

(73) Assignee: IMI Biomed, Inc., San Diego, CA (US)

( * ) Notice: Subject to any disclaimer, the term of this patent is extended or adjusted under 35 U.S.C. 154(b) by 238 days.

(21) Appl. No.: 09/974,942

(22) Filed: Oct. 11, 2001

(65) Prior Publication Data

US 2003/0078194 A1 Apr. 24, 2003

(51) Int. Cl.⁷ .................. A61K 9/127; A61K 38/28; A61K 37/18
(52) U.S. Cl. .................. 424/450; 424/455; 424/456; 424/498; 530/303; 530/306; 530/383; 530/399; 514/2; 514/3
(58) Field of Search ............... 424/450, 455, 424/456, 498, 85.4, 94.1; 530/303, 306, 351, 383, 384, 399; 514/2, 3

(56) References Cited

U.S. PATENT DOCUMENTS

| | | | |
|---|---|---|---|
| 4,615,885 A | * 10/1986 | Nakagame et al. | 424/94 |
| 4,837,028 A | 6/1989 | Allen | 424/450 |
| 4,849,227 A | 7/1989 | Cho | 424/498 |
| 5,552,156 A | 9/1996 | Burke | 424/450 |
| 5,656,289 A | * 8/1997 | Cho et al. | 424/455 |
| 5,665,700 A | 9/1997 | Cho et al. | 514/2 |
| 5,858,398 A | * 1/1999 | Cho | 424/450 |

* cited by examiner

*Primary Examiner*—Jon Weber
*Assistant Examiner*—Abdel A. Mohamed
(74) *Attorney, Agent, or Firm*—Goodwin Procter LLP (57) ABSTRACT

The present invention provides pro-micelle compositions comprising a pharmaceutically active agent encapsulated with a membrane of esterified $C_{12}$–$C_{18}$ fatty acids. In the mammalian intestine, exposure to $C_{12}$–$C_{18}$ fatty acids results in conversion of the pro-micelle to a stable micelle that effectively delivers the pharmaceutically active agent to the systemic circulation. The present invention further provides methods of making and using such compositions.

34 Claims, 11 Drawing Sheets

PRO-MICELLE PHARMACEUTICAL COMPOSITIONS

BACKGROUND OF THE INVENTION

Oral formulations of certain pharmaceutically active agents are subject to degradation and inadequate absorption following administration to mammals. Attempts have been made to improve the stability and bioavailability of orally administered active agents. For example, liposomes and micelles have been used as drug carriers. See, e.g. U.S. Pat. No. 5,552,156 to Burke; U.S. Pat. No. 4,837,028 to Allen. U.S. Pat. No. 4,849,227 to Cho discloses compositions for oral administration comprising particles consisting of an emulsifying agent and a surfactant wherein an active agent is bound to the surface of the particles, and the particles are coated with a lipid coating. U.S. Pat. No. 5,665,700 to Cho et al. discloses a formulation comprising a hydrophilic phase containing a biologically active material wherein the hydrophilic phase is dispersed in a lipophilic phase to form an emulsion. U.S. Pat. No. 5,858,398 to Cho discloses formulations comprising a microparticle of active agent, phospholipid and surfactant wherein the microparticle is suspended in a micelle.

U.S. Pat. No. 4,615,885 to Nakagame et al. discloses a liposome preparation comprising urokinase and higher fatty acids, a polyalkylene glycol and calcium. Nakagame et al. disclose that the higher fatty acids are incorporated into the membrane of liposome at a concentration such that the phospholipid remains in lamella structure. The concentration of fatty acids in the membrane is preferably 5–15% by weight. Higher concentrations result in formation of micelles having the fatty acid at the center, and according to Nakagame et al. will thereby lower or eliminate the ability of the composition to carry the drug.

Micelles are known as drug delivery systems, but generally suffer from poor stability, resulting in separation of the active agent from the micelle. Attempts to promote the absorption of insulin and other macromolecules from the intestine by applying surfactants, triglycerides and lipid-surfactant mixed micelles have generally met with poor results. Muranishi et al. (1978) J. Pharm. Dyn. 1:28; Inouye et al. (1979) J. Pharm. Dyn. 2:286; Danforth et al. (1980) J. Pharm. Dyn. 4:219; Crane et al. (1968) Diabetes 17:625.

U.S. Pat. No. 5,858,398 disclose stabilization of micelles by addition of hydrophilic cholesterol and phospholipids in vitro.

In accordance with the present invention, it has been discovered that encapsulation of a pharmaceutically active agent with a layer of $C_{12}$–$C_{18}$ fatty acids forms a pro-micelle which, upon administration to a mammal, provides a stable micelle. The pro-micelle effectively delivers the pharmaceutically active agent, and does not require stabilization in vitro with cholesterol and phospholipid.

SUMMARY OF THE INVENTION

The present invention provides compositions comprising a pharmaceutically active agent encapsulated within a membrane of $C_{12}$–$C_{18}$ fatty acids, which is further optionally encapsulated within a gelatin capsule. In the mammalian intestine, exposure to $C_{12}$–$C_{18}$ fatty acids results in in vivo formation of a stable micelle that effectively delivers the pharmaceutically active agent into the systemic circulation. The present invention further provides methods of making and using such compositions.

DETAILED DESCRIPTION OF THE INVENTION

The present invention provides pharmaceutical compositions comprising a pharmaceutically active agent encapsulated within a membrane of esterified $C_{12}$–$C_{18}$ fatty acids, which is further optionally encapsulated within a gelatin capsule. Fatty acids are present in the composition in a total concentration of less than 15 weight % so that the composition is in the form of a "pro-micelle." The term pro-micelle as used herein means a composition having a concentration of $C_{12}$–$C_{18}$ fatty acids that is insufficient to form a micelle, but that which is capable of forming a micelle upon exposure to fatty acids in the digestive system of a mammal. In particular, upon administration to a mammal, the pro-micelle is exposed to fatty acids in the intestine such that the total volume percent of fatty acids exceeds 15%, and the pro-micelle forms a micelle.

Formation of a micelle in vivo from the pro-micelles of the present invention provides delivery of the pharmaceutically active agent to the systemic circulation. The agent with the micelle is readily absorbed by the intestinal absorptive systems via the monoglyceride pathways, while the agent in any pro-micelle remaining in the form of a liposome is absorbed via the alpha-glycerol phosphate. In accordance with the present invention, insulin delivered by oral administration in the form of the pro-micelle was found in the lymphatic fluid draining the duodenum (similar to the liposomes of U.S. Pat. No. 5,656, 289 and microemulsion of U.S. Pat. No. 5,665,700) as well as in the portal blood flowing into the liver (similar to the stabilizer micelle of U.S. Pat. No. 5,858,398). Thus, delivery is similar to that observed upon injected insulin. In particular, insulin is delivered to the liver by the formulation of the present invention just as pro-insulin secreted endogenously from the β-cells of the pancreas is delivered.

Pharmaceutically active agents include but are not limited to peptides, glycoproteins, organic and inorganic chemicals, herbals and other materials known in the art to be useful as pharmaceutically active agents. In particular, pharmaceutically active agents that may be employed in the present invention include: (1) peptides such as insulin, growth hormones, interferon, calcitonins, urokinase, coagulation Factor-VIII, coagulation Factor IX, erythoropoietin: (2) compounds having poor bioavailablity and/or compounds for targeted delivery to specific organs or systems, such as nafcillin, vincristin, cephazoline, doxorubicin, quinine, chloroquine, primaquine, d-alpha-tocopherol (which is also an antioxidant), and gentamicin; (3) compounds which, after absorption, are predominantly bound to plasma proteins and/or rapidly biotransformed at the liver, thereby exhibiting poor bioacitivity, such as glyburide, indomethacin, oxyphenbutazone, chlorothiazole, propranolol, cyclophosphamide; and (4) those neuoropharmacologics which mimic sustained intravenous infusion of compounds, preferably those capable of crossing the blood-brain-barrier membrane, such as physostigmine, fluoxetine, and feldene. As will be apparent to those skilled in the art, the choice of agent or agents employed is dependent upon the condition, disease or illness being treated, or the therapy to be employed. In a particular preferred embodiment, the peptide is insulin, and the composition is employed for the treatment of diabetes. In another particularly preferred embodiment, the agent is vincristin, and the composition is employed in cancer treatment. The amount of the pharmaceutically active agent depends upon the nature of the material and intended use, and can be determined by one of ordinary skill in the art.

The pharmaceutically active agent is provided as a core solution within the fatty acid-containing membrane of the pro-micelle of the present invention. The core solution may be a microemulsion or liposome. Preferred microemulsions are disclosed in U.S. Pat. No. 5,665,700 to Cho et al., the disclosure of which is incorporated herein by reference. The microemulsions preferably contain the pharmaceutically active material in association with a phospholipid in the presence of a surfactant. The micro-emulsions may further contain hydrophilic liquids, solvents, protein inhibitors, stabilizers, emulsification acids, preservatives. The microemulsion may be prepared by admixture, or by preparation of hydrophilic and lipophilic phases followed by admixture thereof, and by use of a microfluidizer.

Preferred liposomes are disclosed in U.S. Pat. No. 5,656,289 to Cho et al., the disclosure of which is incorporated herein by reference. The liposomes preferably contain a hydrophilic phase having a pharmaceutically active material and a continuous hydrophilic phase containing cholesterol, phospholipid, lipophilic surfactant and unesterified fatty acid. The liposomes may be prepared by admixing the foregoing ingredients.

The phospholipids in the microemulsions or liposome are preferably water soluble or miscible phospholipids such as glycerophosphates, glycerophosphorylcholines, phosphorylcholines, glycerophosphorylethanolamines, phosphoryl-ethanolamines, ethanolamines, glycerophosphorylserines, and glycerophosphosphorylglycerols.

The phospholipid may be a lysophospholipid such as sn-1-acyl-3-glycerophosphate, sn-1,2-diacylglycerol, sn-1-acyl-glycerophosphoryl-choline, sn-1-diacyl-glycerolphosphate, sn-1-diacyl-3-glycerophosphoryl-ethanol-amine, sn-1,2-acyl-3-glycerophosphorylserine, sn-1,2-acyl-3-glycero-phosphate, sn-1-acyl-3-glecerophosphoryl-glycerol, sn-1,2-diacylglycerophosphate, 1-myristoyl-sn-glycero-3-phosphocholine; 1 myristoyl-sn-glycero-3-phosphoethanolamine; 1-myristoyl-sn-glycero-3-phospho-(N,N-dimethyl)-ethanolamine; 1-palmytoyl-sn-glycero-3-phosphocholine (or ethanolamine), 1-palmitoyl-rac-glycero-3-phos-phocholine, 1-palmitoyl-sn-glycero-3-phospho-(N,N-dimethyl)-ethanolamine; 1 stearoyl-sn-glycero-3-phosphcholine, and mixtures thereof.

The microemulsions or liposomes preferably contain 5 volume % or less of oleic acid and other fatty acids such as ricinoleic acid and linoleic acid. The fatty acids may be saturated or unsaturated. In a preferred embodiment, the fatty acids are unsaturated.

The microemulsion or liposome is encapsulated with a mid-layer containing esterified saturated $C_{12}$–$C_{18}$ fatty acids. The fatty acids may be combined with glycerol or lecithin. The $C_{12}$–$C_{18}$ fatty acids may be extracted from coconut. The mid-layer is preferably about 0.02 nm thick.

The mid-layer may be further encapsulated with film coating to provide a minicapsule. The film coating preferably comprises gelatin and may further comprise glycerol and hydroxylmethyl cellulose. The minicapsules may be packed into gelatin capsules.

The fatty acid concentration in the total composition, including any fatty acid in the core, is less than 15 weight %.

In a preferred embodiment, the mini-capsules have a size of about 1.8–3 mm.

The compositions of the present invention are made by preparing the core solution of the microemulsion or liposome, adding the esterified $C_{12}$–$C_{18}$ fatty acids, and then coating with a film coating. The microemulsion or liposome may be made into a solid powder form, for example, by spray coating over a carrier such as an inert hydroxypropyl cellulose power by using a fluidizer bed or similar equipment such as SPIR-A-FLOW of Freund Co., Ltd., Tokyo, Japan.

The core solution may be coated with the mid-layer of esterified $C_{12}$–$C_{18}$ fatty acids and then the film coating by using a multiple-nozzle apparatus such as the SPHEREX-LABO apparatus by Freund Co., Ltd. In a preferred embodiment, the core solution containing the pharmaceutically active agent is vibrated and sprayed using the SHEREXLABO apparatus at a flow rate of 5 ml/min at a vibration rate of 5.5 and frequency of 20 Hz/sec.; coated with the mid-membrane layer of $C_{12}$–$C_{18}$ fatty acids from coconut (350 g) and soybean lecithin (150 g) by vibrating at 7.4 and a frequency of 20 Hz/sec.; and film coated with a solution containing gelatin (118.7 g), glycerol (19.4 g), sodium hydroxide (5.5 g), hydroxymethyl cellulose (56.4 g) and water (100 g). The resulting minicapsules have a size of 1.8–3.0 mm (mean of 2 mm) and are rapidly hardened by dropping into a 1.5–2.0 ml tube containing cold circulating vegetable oil.

The hardened minicapsules are collected on collecting mesh, washed to remove vegetable oil and dried overnight at 25° C. The dried minicapsules are capsulated into #1 or #2 soft gelatin capsules and contain 16U or 8U, of insulin respectively, and have a total weight of 16.44 mg/capsule. This preferred preparation is summarized as follows:

|  | Wt % | SpGrv | Vol % | 20 Hz/Sec | Minicap |
|---|---|---|---|---|---|
| CORE | 30 | 0.92 | 32.63 | 5.5 | 3.8 mg [23.1%] |
| MID | 40 | 0.918 | 43.59 | 7.4 | 7.65 mg [46.5%] |
| FILM | 30 | 1.262 | 23.78 | 16.9 | 4.99 mg [30.4%] |

The minicapsules containing the promicelles (containing 5% (wt/vol.) of $C_{12}$–$C_{18}$ fatty acids), when administered to a human subject, are protected from the acidic pH in the stomach by the enteric coated film of the minicapsule, and easily passed through the pylorus to the duodenum because of the size of 1.8–3.0 mm. In the intestine, exposure to fatty acids increases the mid membrane fatty acid to greater than 15 weight % and reverses the promicelle to a micelle, which is stable and bioavailable.

The compositions of the present invention are useful for delivering a pharmaceutically active agent to a mammal, and preferably a human. The pharmaceutically active agent is orally administered in the form of an enteric-coated capsule to a mammal, preferably a human, in need of delivery of the agent. In a preferred embodiment, the pharmaceutically active agent is insulin.

All references cited herein are incorporated herein by reference in their entirety.

The following non-limiting examples serve to further illustrate the invention.

EXAMPLE 1

A liquid orally administrable insulin-containing formulation is prepared as follows. All chemicals used in this and the other examples are of analytical or chemical grade.

Sub-Mixture-A is prepared by dissolving the following ingredients in 95% ethanol (about 20 ml) at 40° C. in a water bath:

Glycerol Monooleate (1.5~5.0 g; preferably 2.8~3.2 g),
Lecithin (0.5~6.0 g; preferably 3.0~3.5 g),
Cholesterol (2~8 g; preferably 2.8~4.6 g),
Phosphatidic acid (0.05~0.97 g; preferably 0.15~0.33 g), and
Lysophosphotidyl choline (0~20 g; preferably 3.2~9.8 g)

An Anti-oxidant solution is prepared by dissolving the following ingredients in 95% ethanol (100 ml):

Propyl Gallate (5~25 g; preferably 10~18 g)
Butylated Hydroxy Anisole (3~30 g; preferably 8~14 g)
Butylated Hydroxy Toluene (5~45 g; preferably 10~20 g)

Sub-Mixture-B is prepared by dissolving the following ingredients in 95% ethanol (@150 ml) at 40° C. in a water bath:

Polyoxyethylene-40-Stearate (0.9~5.8 g; preferably 1.5~3.9 g);
Oleic Acid (15.2~66.5 g; preferably 36.5~48.9 g);
Propylparaban (0.89~2.58 mg; preferably 92~118 Mg);
Ascorbic Acid (58~290 mg; preferably 92~121 Mg);
Anti-Oxidant (52~380 mg; preferably 200~340 Mg);
α-Tochopherol (0.9~5.6 g; preferably 2.0~3.9 g);
Methylparaban (482~988 mg; preferably 580~720 Mg);
Sub-Mixture-A (12~48 g; preferably 19~37 g);
making up to 210 g with 95% ethanol and mixing well.

Sub-Mixture C is prepared by dissolving the following ingredients in 35 ml of 95% ethanol: Insulin (a sufficient amount of Insulin to give 8U in #4 size capsule containing about 125 mg of the Insulin containing minicapsules & 16U in #2 size capsule containing about 250 mg of the Insulin containing minicapsules), and aprotinin (sufficient kallikrein inactivator units (KIU) to prevent the above-specified quantities of Insulin from biodegradation by insulinase, peptidase, etc. in vivo). For example, about 1.2 million KIU equivalent aprotinin is added per about 343,200 Units of porcine Insulin. The two ingredients are mixed an the pH adjusted to about 2.4 by adding a concentrated solution of Citric Acid. N-Acetyl Neuraminic Acid (0.8~2.5 g; preferably 0.9~1.8 g) is then added and dissolved, and in a few cases, Cyclohexylurea (Glipizide, etc. at its minute, clinically ineffective doses, e.g., 0.05 mg) is added to supplement the blocking effect of Neuraminic Acid for clearing factors as described by U.S. Pat. No. 4,837,028. All ingredients are dissolved completely by constant stirring, and made up to 70 ml with 95% ethanol.

Sub-Mixture D is prepared by dissolving the following ingredients in about 50 ml of water at 40° C. in a water bath:

Polyoxylene-40-stearate (0.5~2.4 g; preferably 0.88~2.55 g)
Hydroxypropylcellulose (2.55~9.89 g; preferably 3.08~7.04 g)
Sodium benzoate (4.8~14.9 g; preferably 8.69~12.48 g)
and Making up to 70 ml with water.

A microemulsion containing insulin is made by mixing Sub-Mixture B (210 ml), Sub-Mixture C (70 ml), Sub Mixture D (70 ml) and Oleic Acid (5 w % of the Sub-Mixtures B, C, & D), and microfluidizing once in cold by using the microfluidizer of Micro-fluidic Co. of Newton, Mass., U.S.A. at about 100,000~200,000 psi shear force. The microemulsion containing Insulin is made into the mini-capsules (about 1.8~3.2 mm in size) containing the core Insulin containing microemulsion (32.61 vol %; specific gravity of 0.92), which is encapsulated with the mid-layer of membrane made of esterified C12~C18 saturated fatty acids from coconut and lecithin (43.5 vol. %; specific gravity of 0.918), which is further encapsulated with gelatin (118.7 g), glycerin (17.4 g), NaOH (5.5 g), HP-55 (56.4 g), and water (600 g) (outer film layer of 23.77 vol %; specific gravity of 1.262). Each minicapsule contains about 0.01414 ml each and about 0.6 U of Insulin. The doses of Insulin contained in the minicapsule can be adjusted or modified as needed.

EXAMPLE 2

Sub-Mixture-A is prepared by dissolving the following ingredients in about 60 of 95% ethanol, and then making up to 100ml with 95% ethanol:

Polyoxyethylene-40-stearate (1~7 g; preferably 3.5~4.6 g);
Sodium Benzoate (0.4~5.4 g; preferably 1.8~3.2 g);
Aprotinin (as described in EXAMPLE 1);
Nonulosaminic acid (0.05~6.0 g; preferably 0.4~1.0 g);
Sodium Benzoate (0.5~5.8 g; preferably 1.8~4.2 g);
Hydroxy Propyl Cellulose (3.8~14.2 g; preferably 5.4~8.8 g)

Sub-Mixture B is prepared by dissolving insulin as in Example 1, and adjusting the pH to 2.4 with a concentrated Citric Acid and Ascorbic Acid, and making up to a final volume of 100 ml with 95% ethanol.

Sub-Mixture-C is prepared by mixing Sub-Mixture-A (100 ml) and Sub-Mixture-B (100 ml).

Sub-Mixture-D is prepared by heating: 125 ml of 95% ethanol to 35~40°,C. and dissolving the following ingredients:

insulin levels were measured at time 0, 1.5 & 2.5 hours after taking the oral insulin. Results are shown in Table I and FIGS. 4 and 5.

TABLE I

| PTS | AGE | SEX | Blood Glucose (mMol/L) | | | | | Serum Concentration of insulin (uU/Ml) | | |
|---|---|---|---|---|---|---|---|---|---|---|
| | | | 0 | 1 | 2 | 3 | 4 | 0 | 1.5 | 2.5 Hrs |
| 1 | 44 | F | 10.5 | 10.3 | 5.8 | 6.6 | 6.7 | 9.8 | 141 | 160.4 |
| 2 | 35 | F | 8.9 | 8.2 | 3.7 | 6 | 4.9 | 11.4 | 46.5 | 201 |
| 3 | 40 | M | 11.1 | 9.5 | 8.2 | 5 | 5.8 | 13.7 | 87.6 | 186.6 |
| 4 | 55 | M | 9.2 | 8.2 | 5.7 | 5.1 | 4.2 | 7.9 | 76.9 | 179.1 |
| 5 | 56 | F | 8.6 | 8.1 | 6.2 | 5.4 | 3.8 | 14 | 88 | 108 |
| 6 | 63 | M | 7.8 | 6.9 | 5.8 | 4.7 | 4.8 | 26 | 72 | 161.9 |
| 7 | 38 | M | 6.2 | 5.9 | 6.1 | 4.5 | 4.5 | 22.2 | 83.1 | 179 |
| MEAN | 47.29 | 4M; 3F | 8.90 | 8.16 | 5.93 | 5.33 | 4.96 | 15.00 | 85.01 | 168.00 |
| SEM | 10.67 | | 1.64 | 1.48 | 1.31 | 0.74 | 0.99 | 6.66 | 28.50 | 29.93 |

Cholesterol (2~21 g; preferably 12~21 g);

GlyceroPhosphotidylCholine (3.72~14.65 g; preferably 7.68~11.05 g);

α-Tochopherol (0.05~2.5 g; preferably 0.2~0.9 g);

GlyceroMonoOleate (6.5~18.3 g; preferably 11.42~16.92 g);

LysoPhosphotidylCholine (0~20 g; preferably 3.2~9.8 g); and cooling to room temperature.

Sub-Mixture-E is prepared by heating: 127.2 ml of MCT™ (Medium Chained Triglycerides), Eli Lilly and Co., Indianapolis, Ind.) oil to 35~40°, C. and dissolving the following ingredients:

Tween-80 (0.3~37 g; preferably 0.8~2.1 g);

Propyl Paraben (0.05~5.2 g; preferably 0.08~0.3 g);

Methyl paraben (0.05~3.8 g; preferably 0.8~1.7 g);

Anti-Oxidant (0.08~1.8 g; preferably 0.8~1.9 g) (as described in the Example-1 above); mixing well and cooling to room temperature.

Sub-Mixture-F is prepared by mixing Sub-Mixture-D and cooling to room temperature.

The final formulation is prepared by adding Sub-Mixture-C into Sub-Mixture-F under constant stirring, and homogenizing well with 5 vol % (Sub-Mixture-C & Sub-Mixture-F) of Oleic Acid.

The resulting insulin-containing solution was made into minicapsules of about 3 mm as described in Example 1.

EXAMPLE 3

A total of seven insulin antibody negative diabetics (five Type-2 NIDDM diabetics who were not responding to daily oral doses of sulfonyloreas, e.g. Glyburide and two Type-1 IDDM diabetics), aged from 35 to 63 years old (average age of 47.3 years old), of which four were male and three were female, gave written consent and were admitted to the study center.

Figure 1:
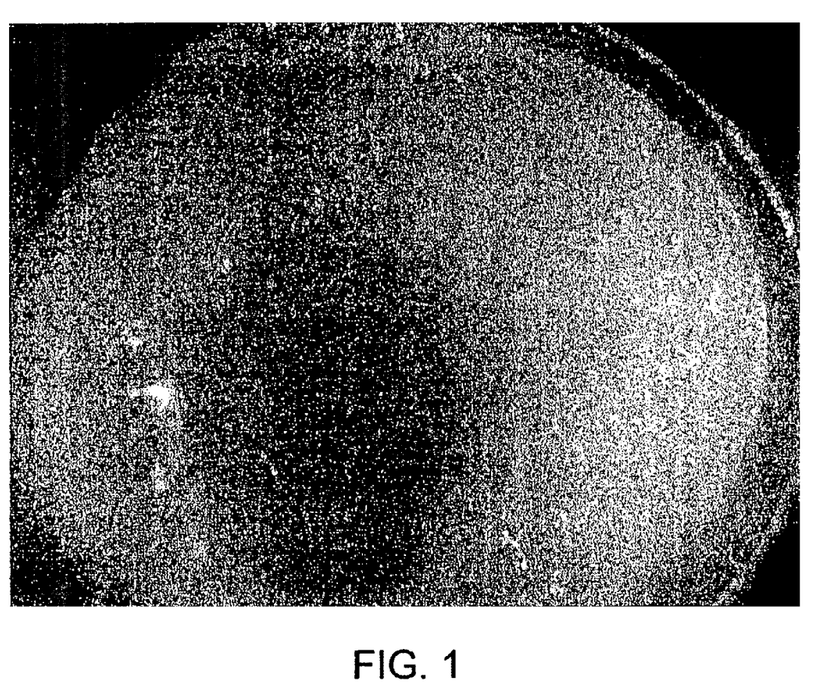
FIG. 1 is a photomicrograph of an insulin-containing micelle (about 0.0141 ml) encapsulated with a 27 μm thick layer of $C_{12}$–$C_{18}$ fatty acids, and further coated with a thin layer of gelatin membrane.
Figure 2:
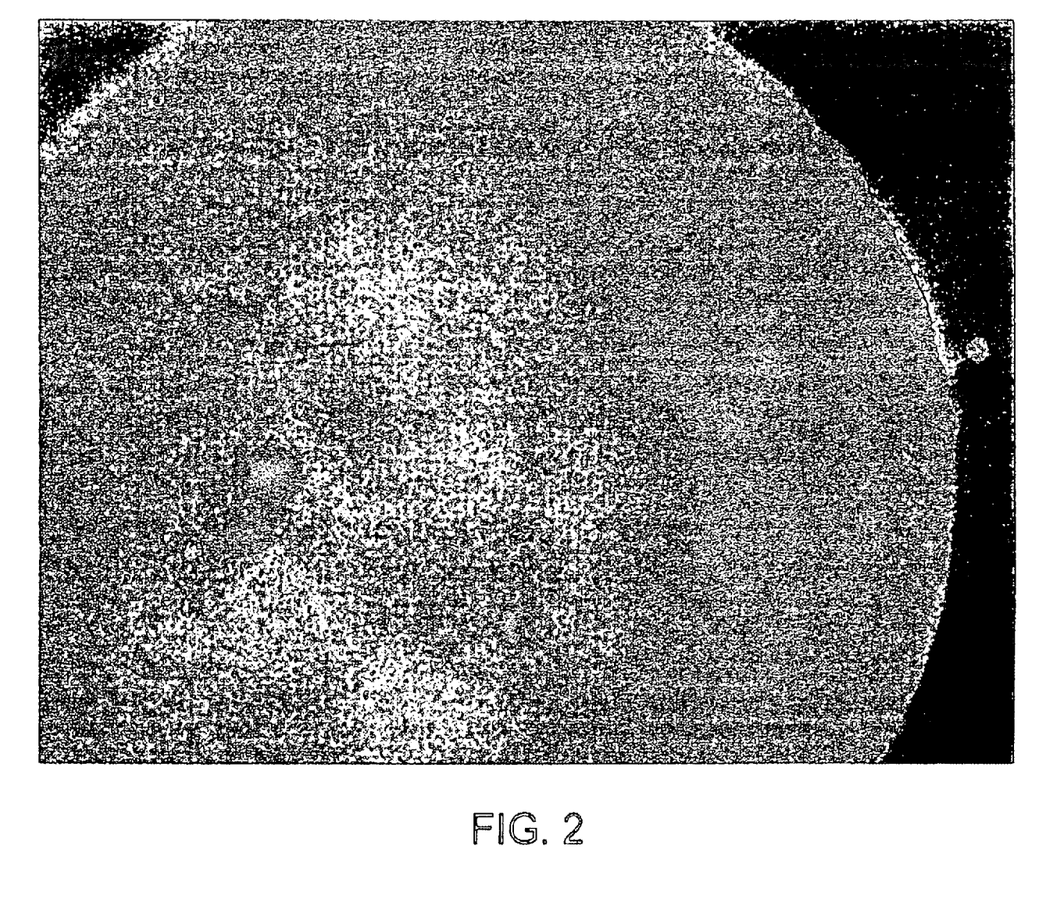
FIG. 2 is a photomicrograph of an insulin-containing micro-emulsion (about 0.0141 ml) encapsulated with a 27 μm thick layer of $C_{12}$–$C_{18}$ fatty acids, and further coated with a thin layer of gelatin membrane.
Figure 3:
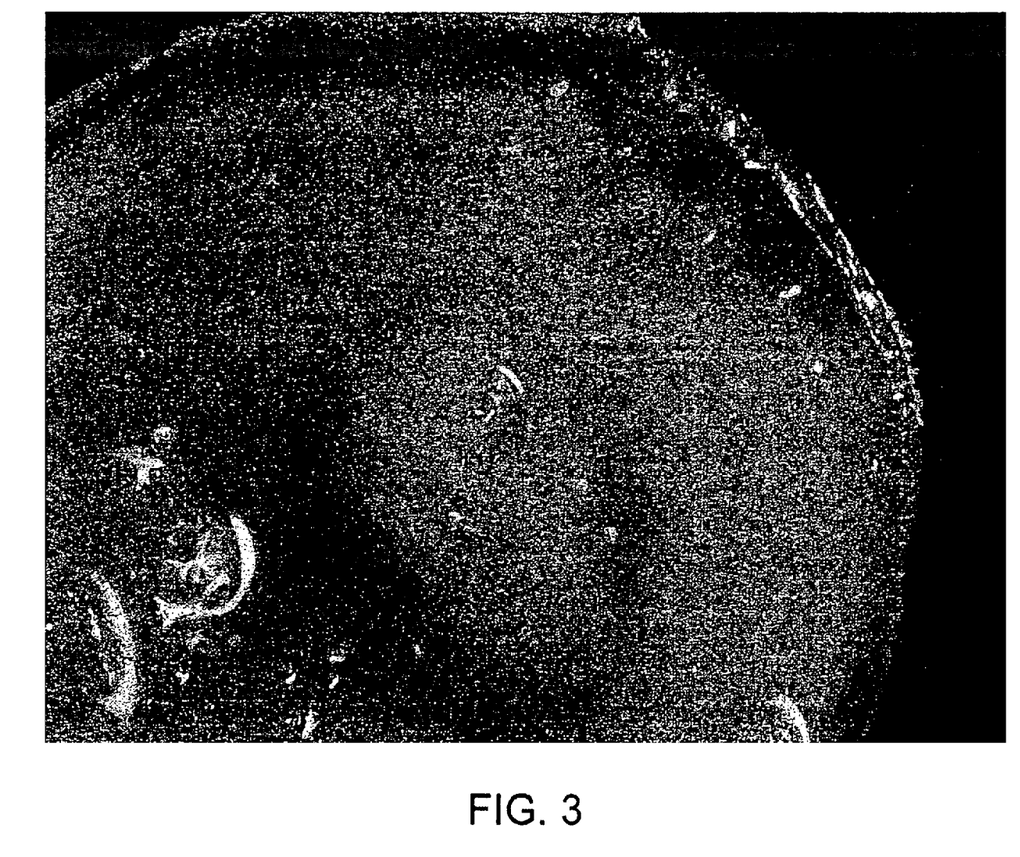
FIG. 3 is a photomicrograph of an insulin-containing liposome (about 0.0141 ml) encapsulated with a 27 μm thick layer of $C_{12}$–$C_{18}$ fatty acids, and further coated with a thin layer of gelatin membrane.
Figure 4:
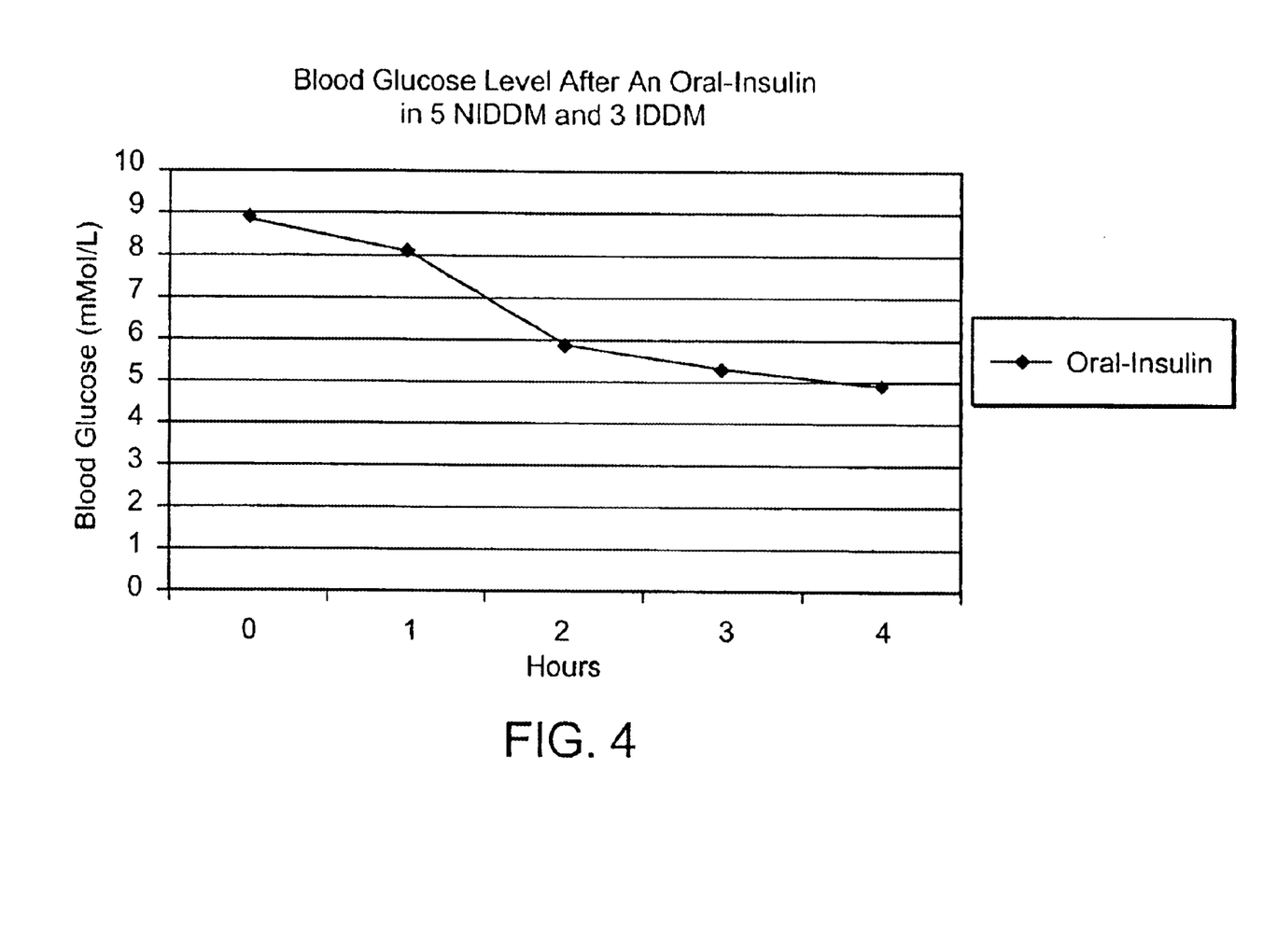
FIG. 4 is a graph depicting blood glucose levels in diabetic patients after administration of the formulation of Example 1.
Figure 5:
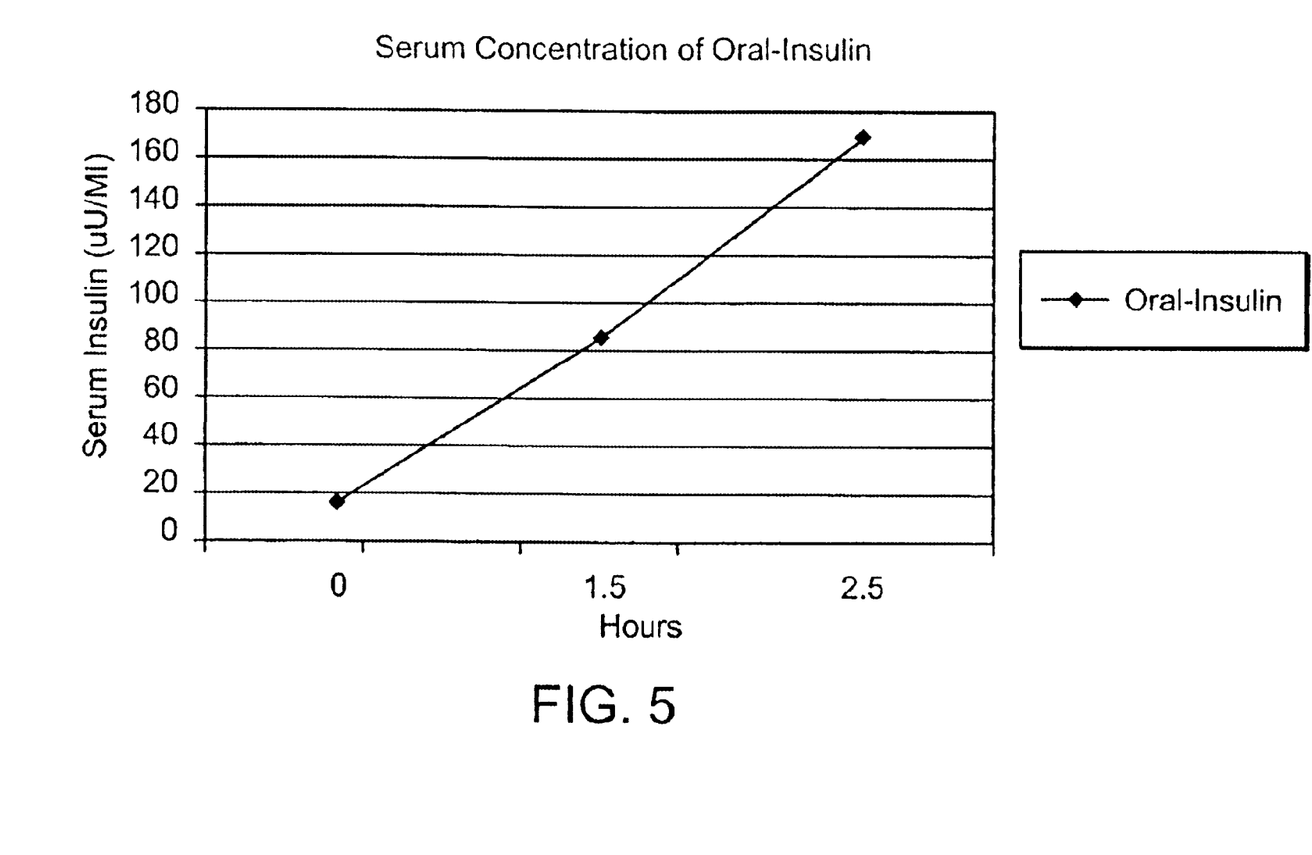
FIG. 5 is a graph depicting serum concentration of insulin in diabetic patients after administration of the formulation of Example 1.

The patients were given a standard diabetic dinner at 6:00~6:30 PM the night before the study day, after which these patients were fasted overnight, except water was given freely. At 6:00 AM on the day of the study, each patient was asked to take the Example-1 form of the minicapsules containing Insulin (approximately 0.5~0.8 U of Insulin per body weight in Kg) with 300 ml of a warm but not hot water. Venous blood samples were collected hourly for four hours for the measurements of blood glucose levels, and the serum As indicated in FIGS. 4 and 5, the blood sugar was gradually reduced to clinically acceptable levels, while the serum insulin levels were increased from the insulinopenic stage in these diabetics to about 168 μUnits per ml. In no cases were severe degrees of hypoglycemia or hyperinsulinemia observed. Such a finding is significantly different from the usually observed responses in blood sugar and serum insulin levels after a subcutaneous injection of insulin in these diabetics, and after administration of therapeutic doses of the liposome or microemulsion-bound formulations of the oral insulin described in U.S. Pat. No. 5,665,700; U.S. Pat. No. 4,849,227, and U.S. Pat. No. 5,656,289). The findings are grossly similar to the clinical data found after administration of the micelle form of oral insulin described in U.S. Pat. No. 5,858,398 except that, in general, a relatively faster onset of pharmacological action in lowering the blood sugar levels have been observed with this new pro-micelle formulation.

EXAMPLE 4

In an anesthetized pig (male; 70 Kg), the duodenum was exposed by a midline incision of the abdomen, and the major largest lymphatic vessel draining from the duodenum was cannulated. Lymph fluid was collected into a mass glass cylinder every 15 minutes for the entire duration of the study. Another catheter was inserted into the portal vein and portal venous blood was sampled every 15 minutes for the duration of the study. Mini-capsules containing insulin as described in Example 2 (2500 mg containing about 160 U of porcine insulin) were soaked overnight in 50 ml cold buffer solution at pH about 2.8 overnight and made into an 'emulsion' which was infused into the duodenum within five minutes through a catheter. Bile flow was not disturbed during the procedure.

Figure 6:
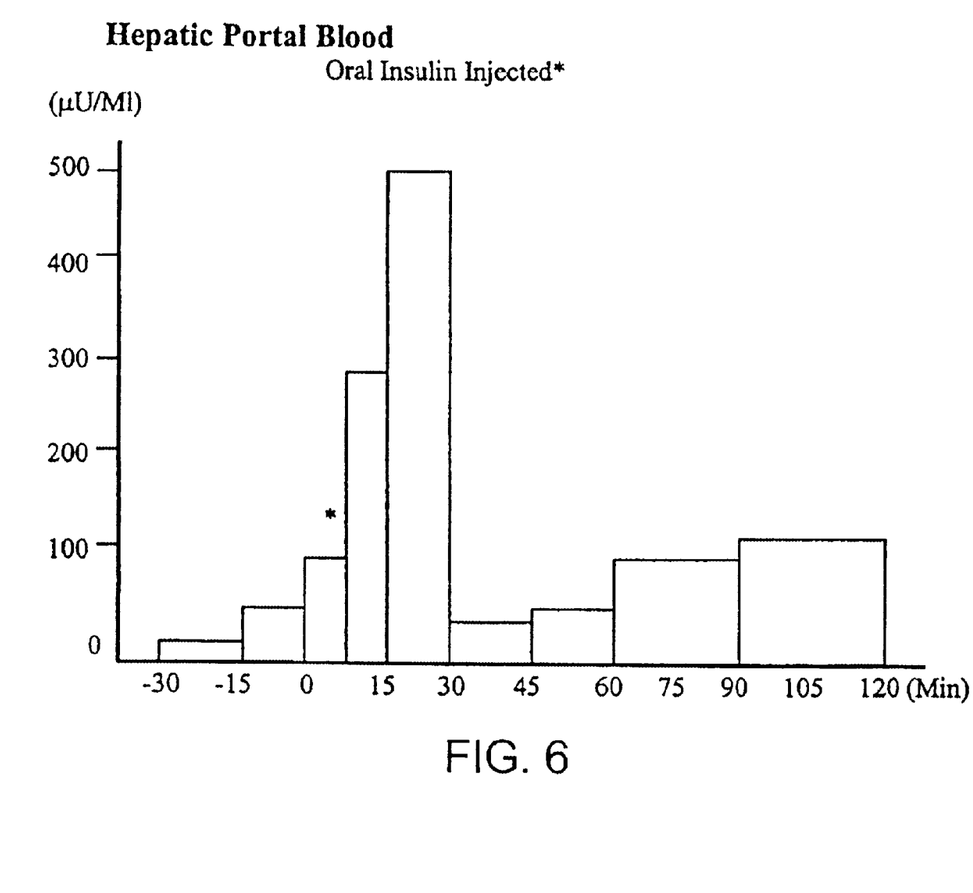
FIG. 6 is a graph depicting insulin concentration in hepatic portal blood after intra-duodenal infusion of the pro-micelle formulation of the present invention.
Figure 7:
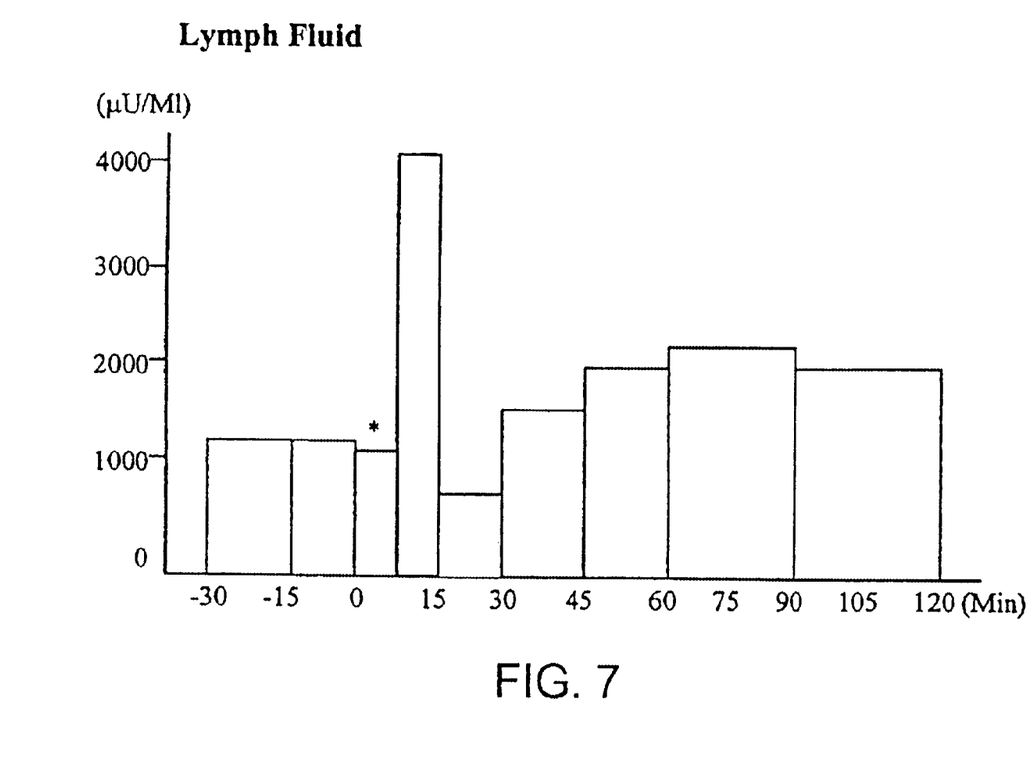
FIG. 7 is a graph depicting insulin concentrations in lymph fluid after intra-duodenal infusion of the pro-micelle formulation of the present invention.
Figure 8:
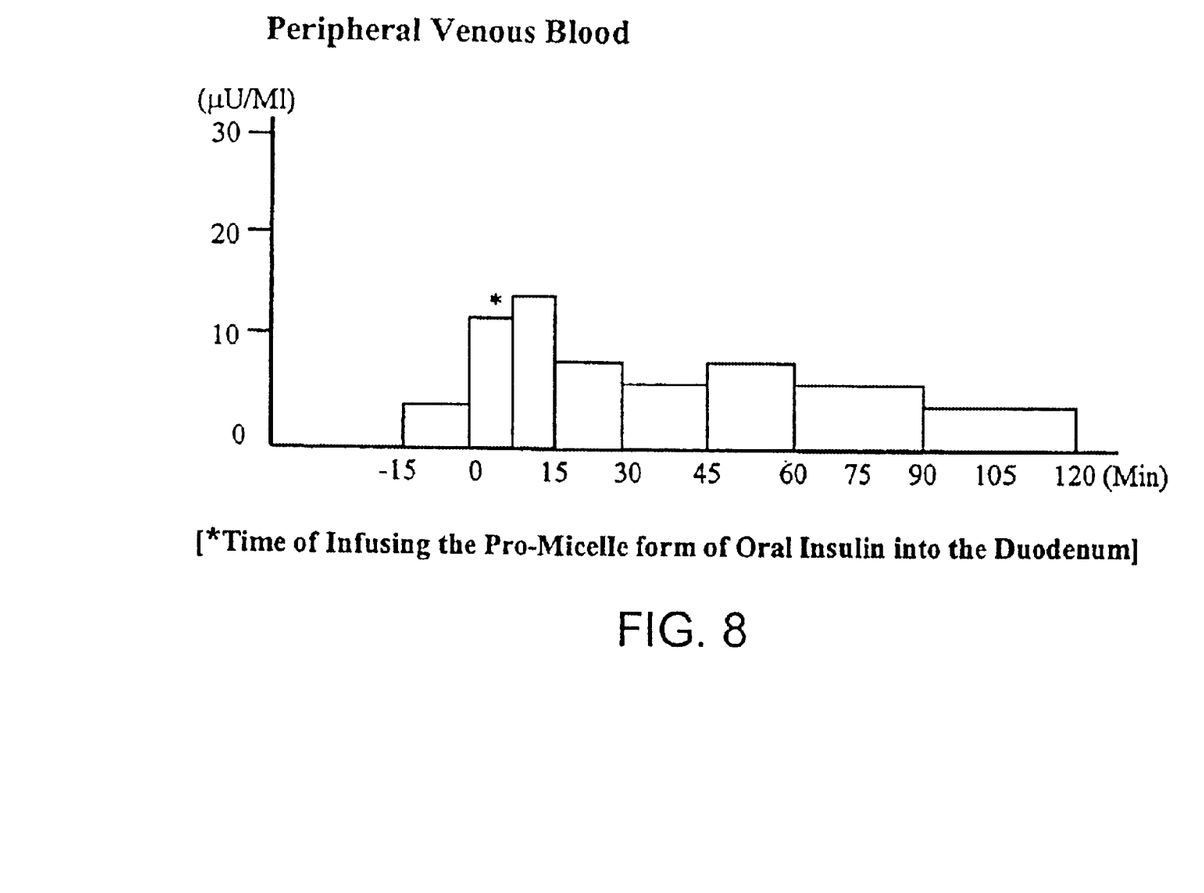
FIG. 8 is a graph depicting insulin concentrations in peripheral venous blood after intra-duodenal infusion of the pro-micelle formulation of the present invention.

The lymph fluids, diluted to 1/10~1/50, and the serum samples were analyzed for insulin concentrations by using an assay method developed by the present inventors, and validated by the bioassay method or the radio-immunoassay method of Novo-Nordisk Diagnostics, LTD, Cambridge, U.K. FIGS. 6, 7 and 8 show insulin concentrations in hepatic portal blood, lymph fluid and peripheral venous blood, respectively.

From earlier studies (U.S. Pat. No. 5,858,398 to Cho) it was shown that the Micelle-bound insulin was predominantly absorbed from the gastrointestinal system via the monoglyceride pathways, and channeled into the liver via the portal venous system (Clark, B & Hubscher, G., Nature 185: 35, 1960; Imai, Y. & Sakagami, T:, in Lipid Biochemistry, pp. 111–126, 1966, Asakura Shoten, Tokyo, Japan). The present study in the pig demonstrated that the some of the oral insulin in a formulation of the present invention infused into the duodenum was found in the portal blood, a significantly higher concentration of the insulin infused into the duodenum was found in the cannulated duodenal lymphatic fluids within 15–30 minutes of the dosing, and some of it was found in the peripheral venous blood.

EXAMPLE 5

Figure 9:
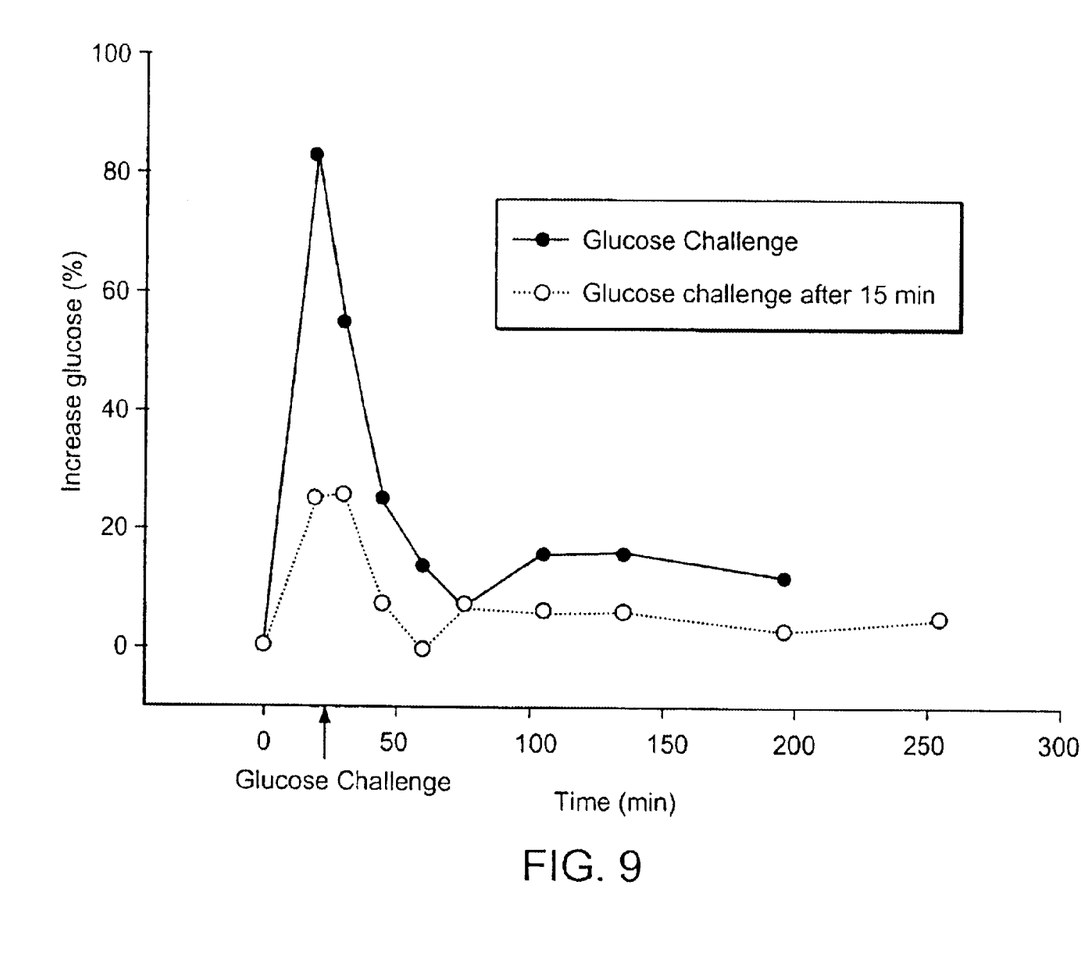
FIG. 9 is a graph depicting increase in blood glucose after intravenous (i.v.) administration of glucose to rabbits.

Capsules containing the pro-micelle form of insulin were prepared using microemulsions as the core generally as described in Example 1. Each capsule contained 4.3U bovine insulin. One capsule was orally administered to each of five albino rabbits of both sexes (3 male, 2 female) weighing between 2.1 and 2.5 kg., 15 minutes before an intravenous glucose challenge of 250 mg/kg. Water was used as the control. As shown in FIG. 9, oral administration of the pro-micelle insulin formulation effectively blocked the hyperglycemia induced by the intravenous glucose administration. Blood glucose was measured by the method of Folin et al., J. Bio. Chem. 38:81, 1919.

Figure 10:
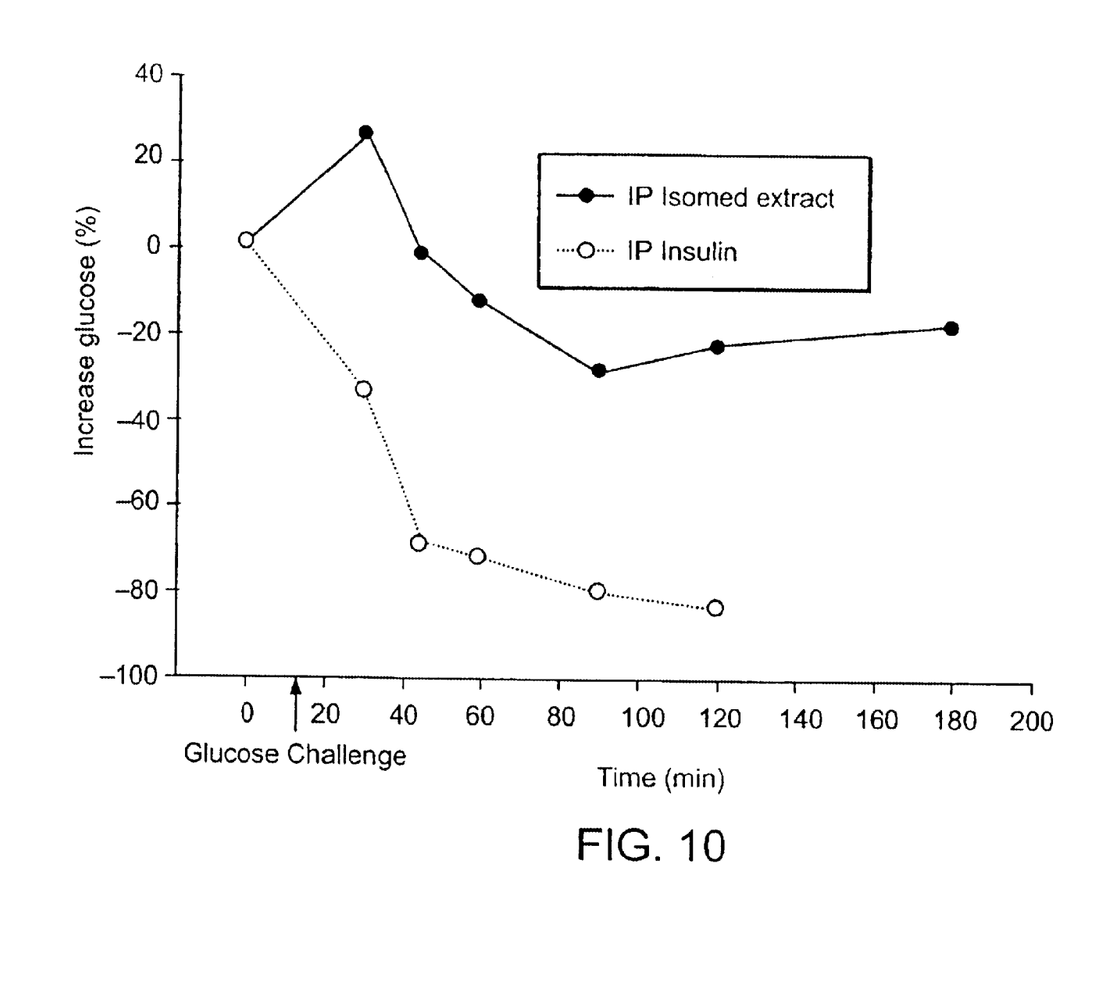
FIG. 10 is a graph comparing blood glucose in response to intraperitoneal (i.p.) administration of standard regular insulin and the formulation of the invention.

FIG. 10 depicts blood glucose when a standard regular insulin solution (0.3 ml of 3.1 IU/ml) or an extraction of the pro-micelle (2.5 ml of 0.4 IU/ml) was administered intraperitonally (i.p.) to rabbits 15 minutes before a glucose challenge of 250 mg/kg. The i.p. injection of standard regular insulin decreased blood sugar. The i.p. injection of the formulation of the invention, which contained minute quantities of sialic acid and cyclohexylurea, effectively modified the hypoglycemia induced by insulin. This indicates that sialic acid and cyclohexylurea block the phagocytic activities of the reticuloendothelial system, including the peritoneum, liver, spleen, kidneys and lungs, and phagocytic cells including monocytes and lymphocytes.

Figure 11:
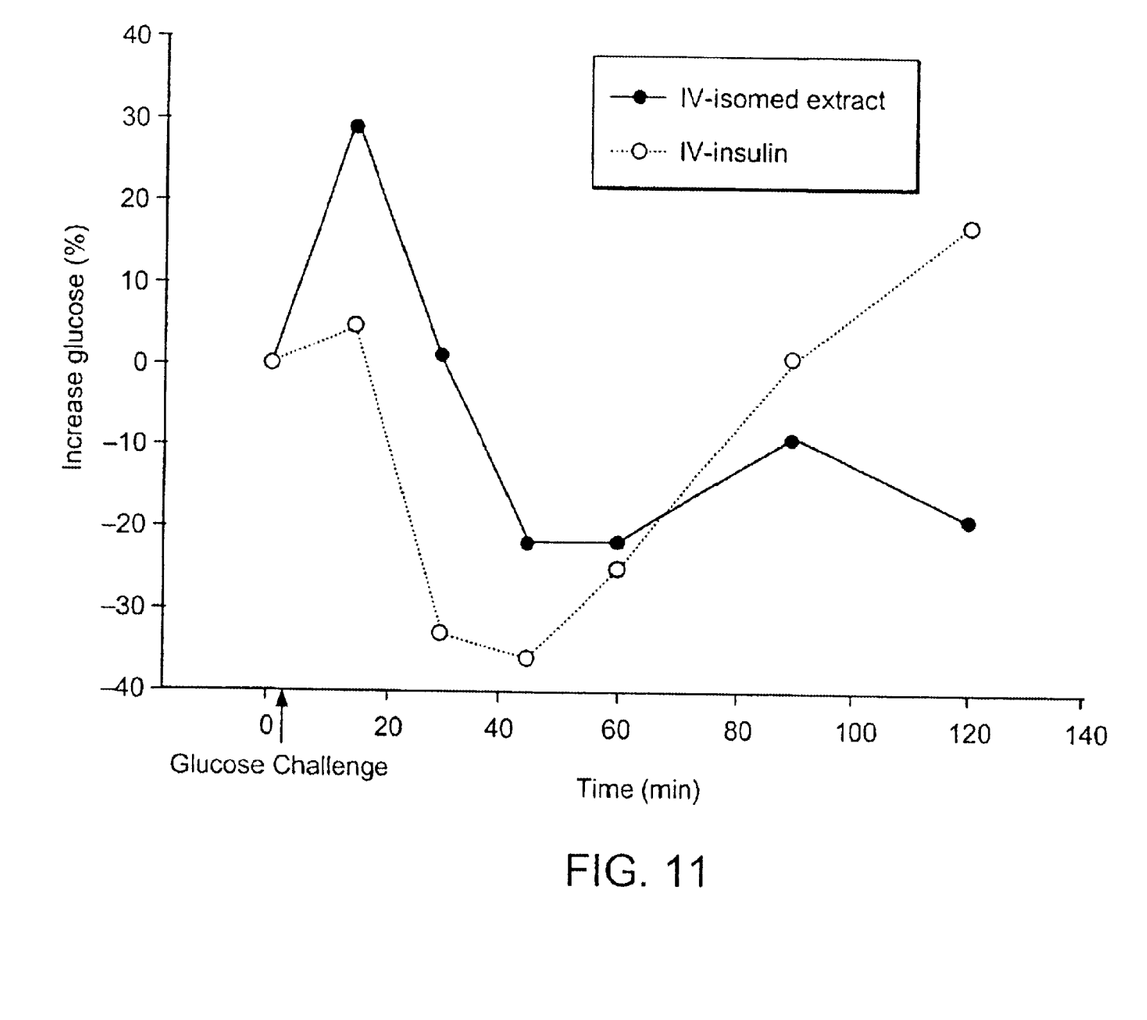
FIG. 11 is a graph comparing blood glucose in response to i.v. administration of standard regular insulin and the formulation of the invention.

FIG. 11 depicts blood glucose levels when a standard regular insulin (0.2 ml of 3.1 IU/ml) or an extraction of the pro-micelle (1.5 ml. of 0.4 IU/ml) was intravenously (i.v.) injected into rabbits one minute before a glucose challenge of 250 mg/kg. With standard regular insulin, blood glucose rapidly decreased from 20 to 45 minutes, then gradually increased until it was from 10–30% of the control level within 90 minutes of the insulin injection. The hypoglycemic effect was short in duration. With the formulation of the invention, a hypoglycemic effect was noticed within 35 minutes, and lasted for the duration of the experiment of 120 minutes or more. The onset was slower and duration longer than for regular insulin.

We claim:

1. A composition comprising a core containing a pharmaceutically active agent wherein the core is encapsulated with a membrane comprising esterified $C_{12}$–$C_{18}$ fatty acids to form a pro-micelle wherein the concentration of fatty acids in the composition is less than 15 weight %.

2. The composition of claim 1 wherein the pharmaceutically active agent is insulin, growth hormone, interferon, calcitonin, urokinase, coagulation Factor-VIII, coagulation Factor IX, erythroporetin, nafcillin, vincristin, cephazoline, doxorubicin, quinine, chloroquine, primaquine, d-alpha-tocophenol, gentamicin, glyburide, indomethacin, oxyphenbutazone, chlorothiazole, propranolol, cyclophosphamide, physostigmine, fluoxetine or feldene.

3. The composition of claim 1 wherein the pharmaceutically active agent is insulin.

4. The composition of claim 1 wherein the $C_{12}$–$C_{18}$ fatty acids are extracted from coconut.

5. A method of delivering a pharmaceutically active agent to a mammal comprising orally administering the composition of claim 1 to said mammal.

6. The method of claim 5 wherein said mammal is a human.

7. The composition of claim 1 wherein the core is a microemulsion or liposome.

8. The composition of claim 7 wherein the microemulsion contains a phospholipid and a surfactant.

9. The composition of claim 7 wherein the lipsome contains a hydrophilic phase containing the pharmaceutically active agent and a continuous hydrophilic phase containing cholesterol, phospholipid, lipophilic surfactant and unesterified fatty acid.

10. The composition of claim 1 wherein the membrane is further encapsulated with a film coating.

11. The composition of claim 10 wherein the film coating comprises gelatin.

12. The composition of claim 10 which is a minicapsule having a diameter of about 1.8 to 3.0 millimeters.

13. The composition of claim 12 which is further coated with an enteric coating.

14. A method of making a composition comprising a pharmaceutically active agent comprising the steps of:
   (a) providing a liposome or microemulsion containing a pharmaceutically active agent;
   (b) coating the liposome or microemulsion with a midlayer comprising esterified $C_{12}$–$C_{18}$ saturated fatty acids to form a pro-micelle; and
   (c) coating said midlayer with a film layer to provide a minicapsule.

15. The method of claim 14 further comprising the step of capsulating said minicapsule into a gelatin capsule.

16. The method of claim 14 wherein said lipsome or microemulsion is in dry powder form.

17. The method of claim 14 wherein said minicapsule has a diameter of from about 1.8 to 3.0 millimeters.

18. A composition comprising a core containing a pharmaceutically active agent wherein the core is encapsulated with a membrane about 0.02 mm thick comprising esterified $C_{12}$–$C_{18}$ fatty acids to form a pro-micelle wherein the concentration of fatty acids in the composition is less than 15 weight %.

19. The composition of claim 18 wherein the pharmaceutically active agent is insulin, growth hormone, interferon, calcitonin, urokinase, coagulation Factor-VIII, coagulation Factor IX, erythroporetin, nafcillin, vincristin, cephazoline, doxorubicin, quinine, chloroquine, primaquine, d-alpha-tocophenol, gentamicin, glyburide, indomethacin, oxyphenbutazone, chlorothiazole, propranolol, cyclophosphamide, physostigmine, fluoxetine or feldene.

20. The composition of claim 18 wherein the pharmaceutically active agent is insulin.

21. The composition of claim 18 wherein the $C_{12}$–$C_{18}$ fatty acids are extracted from coconut.

22. A method of delivering a pharmaceutically active agent to mammal comprising orally administering the composition of claim 18 to said mammal.

23. The method of claim 22 wherein said mammal is a human.

24. The composition of claim 18 wherein the core is a microemulsion or liposome.

25. The composition of claim 24 wherein the microemulsion contains a phospholipid and a surfactant.

26. The composition of claim 24 wherein the lipsome contains a hydrophilic phase containing the pharmaceutically active agent and a continuous hydrophilic phase containing cholesterol, phospholipid, lipophilic surfactant and unesterified fatty acid.

27. The composition of claim 18 wherein the membrane is further encapsulated with a film coating.

28. The composition of claim 27 wherein the film coating comprises gelatin.

29. The composition of claim 27 which is a minicapsule having a diameter of about 1.8 to 3.0 millimeters.

30. The composition of claim 29 which is further coated with an enteric coating.

31. A method of making a composition comprising a pharmaceutically active agent comprising the steps of:

(a) providing a liposome or microemulsion containing a pharmaceutically active agent;

(b) coating the liposome or microemulsion with a midlayer about 0.02 mm thick comprising esterified $C_{12}$–$C_{18}$ saturated fatty acids to form a pro-micelle; and (c) coating said midlayer with a film layer to provide a minicapsule.

32. The method of claim 31 further comprising the step of capsulating said minicapsule into a gelatin capsule.

33. The method of claim 31 wherein said lipsome or microemulsion is in dry powder form.

34. The method of claim 31 wherein said minicapsule has a diameter of from about 1.8 to 3.0 millimeters.

* * * * *